(12) United States Patent
Valussi et al.

(10) Patent No.: US 8,097,140 B2
(45) Date of Patent: Jan. 17, 2012

(54) LIQUID SAMPLE ANALYSIS METHODS

(75) Inventors: Silvia Valussi, London (GB); Andreas Manz, London (GB)

(73) Assignee: Forensic Science Service Ltd., London (GB)

( * ) Notice: Subject to any disclaimer, the term of this patent is extended or adjusted under 35 U.S.C. 154(b) by 1165 days.

(21) Appl. No.: 11/811,101

(22) Filed: Jun. 8, 2007

(65) Prior Publication Data
US 2007/0240990 A1    Oct. 18, 2007

Related U.S. Application Data

(63) Continuation of application No. 10/463,647, filed on Jun. 17, 2003, now abandoned.

(30) Foreign Application Priority Data

Jun. 18, 2002  (GB) .................................. 0213979.8

(51) Int. Cl.
*G01N 27/447*  (2006.01)
(52) U.S. Cl. ........................ 204/454; 204/455
(58) Field of Classification Search .......... 204/450–455, 204/600–605
See application file for complete search history.

(56) References Cited

U.S. PATENT DOCUMENTS

| | | | |
|---|---|---|---|
| 5,089,099 A * | 2/1992 | Chien et al. | 204/453 |
| 5,275,710 A | 1/1994 | Gombocz et al. | |
| 5,302,264 A | 4/1994 | Welch et al. | |
| 5,660,703 A | 8/1997 | Dasgupta | |
| 5,858,195 A | 1/1999 | Ramsey | |
| 5,958,202 A | 9/1999 | Regnier et al. | |
| 6,319,379 B1 | 11/2001 | Davidson et al. | |
| 6,475,441 B1 | 11/2002 | Parce et al. | |
| 6,613,580 B1 | 9/2003 | Chow et al. | |
| 6,695,009 B2 | 2/2004 | Chien et al. | |
| 6,749,735 B1 | 6/2004 | Le Febre | |
| 6,764,817 B1 | 7/2004 | Schneider | |
| 7,005,050 B2 | 2/2006 | Burns et al. | |
| 7,060,171 B1 | 6/2006 | Nikiforov et al. | |
| 2002/0003089 A1 | 1/2002 | DeVault | |
| 2003/0186255 A1 | 10/2003 | Williams et al. | |
| 2005/0161326 A1 | 7/2005 | Morita et al. | |

OTHER PUBLICATIONS

Cooper, J. et al., "Gel Protein Capillary Extraction Apparatus. Electronic Protein Transfer," *Analytical Chemistry*, vol. 74, No. 5, pp. 1182-1186 (Mar. 1, 2002).

Guttman, A., "Sample Stacking during Membrane-Mediated Loading in Automated DNA Sequencing," *Anal. Chem.*, vol. 71, No. 16, pp. 3598-3602 (Aug. 15, 1999).

(Continued)

*Primary Examiner* — Alex Noguerola
(74) *Attorney, Agent, or Firm* — Merchant & Gould P.C.

(57) ABSTRACT

A method for collecting an analyte species from a sample is provided, the method of collection potentially being supplemented to give a method of preparing a sample for analysis and/or a method of analysis. The method including providing part of a sample in a substrate, causing the sample to migrate to an interface between the substrate and a second substrate due to the action of an electrical potential difference, the electrophoretic velocity of the analyte species of the second substrate being balanced by or exceeded by the bulk flow velocity of the second substrate and the bulk flow velocity of the second substrate being in an opposing direction to the electrophoretic velocity of the analyte species in the second substrate. In this way substantial concentration of the analyte species at the interface is provided. Subsequently the species can be conveyed away from the interface for further preparation and/or analysis.

24 Claims, 3 Drawing Sheets

OTHER PUBLICATIONS

Li, J. et al., "Rapid and sensitive separation of trace level protein digests using microfabricated devices coupled to a quadrupole— time-of-flight mass spectrometer," *Electrophoresis 2000*, vol. 21, No. 1, pp. 198-210 (Jan. 2000).

* cited by examiner

LIQUID SAMPLE ANALYSIS METHODS

This application is a Continuation of U.S. patent application Ser. No. 10/463,647 filed on Jun. 17, 2003 now abandoned.

This invention concerns improvements in and relating to analysis, particularly to aspects of the collection of samples and/or preparation of samples.

A variety of situations in medical diagnostics, pharmaceutical industries and forensic science require as high a possible recovery of analyte species from a sample and the provision of those analyte species in as concentrated a form as possible.

Improvements in the efficiency of collection are desirable to extend the range of applications to which subsequent analysis techniques can be applied. Furthermore, improvements which provide a high concentration of the analyte species in the prepared sample can give rise to increased accuracy and/or speed and/or simplification in subsequent analysis techniques.

In the context of forensic sciences achieving the above mentioned aims would allow improved identification and analysis of biochemical markers in biological materials, and particularly allow the chemical composition of fingerprints to be analysed.

According to a first aspect of the invention we provide a method of collecting an analyte species from a sample, the method including:
  introducing at least a part of the sample to a substrate, the substrate having an interface with a second substrate;
  applying an electrical potential difference across at least a part of the substrate, the interface and at least a part of the second substrate, at least one of the analyte species in the substrate moving towards the interface as a result of the electrical potential difference to form collected analyte species;
  and wherein the electro-phoretic velocity of the analyte species in the second substrate is balanced by or exceeded by the bulk flow velocity of the second substrate and the bulk flow velocity of the second substrate is in an opposing direction to the electrophoretic velocity of the analyte species in the second substrate.

According to a second aspect of the invention we provide a method of preparing a sample for analysis, the method including:
  collecting an analyte species from a sample by introducing at least a part of the sample to a substrate, the substrate having an interface with a second substrate;
  applying an electrical potential difference across at least a part of the substrate, the interface and at least a part of the second substrate, at least one of the analyte species in the substrate moving towards the interface as a result of the electrical potential difference to form collected analyte species;
  the electrophoretic velocity of the analyte species in the second substrate being balanced by or exceeded by the bulk flow velocity of the second substrate, the bulk flow velocity of the second substrate being in an opposing direction to the electrophoretic velocity of the analyte species in the second substrate;
  the method further including reversing the electrical potential difference across the at least a part of the substrate, the interface and the at least part of the second substrate, the collected analyte species moving away from the interface and through the second substrate as a result of the electrical potential difference being reversed.

According to a third aspect of the present invention we provide a method of analysing an analyte species from a sample, the method including:
  collecting the analyte species from a sample by introducing at least a part of the sample to a substrate, the substrate having an interface with the second substrate;
  applying an electrical potential difference across at least a part of the substrate, the interface and at least a part of the second substrate, at least one of the analyte species in the substrate moving towards the interface as a result of the electrical potential difference to form collected analyte species;
  the electrophoretic velocity of the analyte species in the second substrate being balanced by or exceeded by the bulk flow velocity of the second substrate, the bulk flow velocity of the second substrate being in an opposing direction to the electrophoretic velocity of the analyte species in the second substrate;
  the method further including reversing the electrical potential difference across the at least a part of the substrate, the interface and the at least part of the second substrate, the collected analyte species moving away from the interface and through the second substrate as a result of the electrical potential difference being reversed;
  and wherein the analyte species in the second substrate being fed to an analysis stage, one or more pieces of information being determined about the analyte species by the analysis stage.

The first and/or second and/or third aspects of the invention may include any of the following features, options or possibilities.

The analyte species may be one or more of a disease marker, a protein, a drug, a metabolite, a bio-chemical marker, a chemical residue, a chemical component of fingerprint or other body marks, a skin residue or an excretion or a plurality of such species or of different types of the same species.

The sample may be a blood sample, bodily fluid sample, a sample obtained by contact with the body or pre-prepared part of a body.

The substrate may be a gel, a polymer or porous membrane.

The at least part of the sample may be provided in the substrate by introducing the sample into the substrate or introducing the sample to a surface of the substrate. Preferably a part of the substrate removed from the interface receives the at least part of the sample. The sample may be provided in the substrate by contacting a part of the persons body with the substrate, for instance applying a fingertip, particularly the print thereof, to the substrate surface.

The second substrate may be a liquid volume, such as a buffer.

The second substrate may be a gel, polymer or porous membrane of a different conductivity to the substrate.

Preferably the interface between the substrate and the second substrate is provided on an opposing side of the substrate to the surface to which the sample is introduced. The interface may have a smaller surface area than one or more other surfaces of the substrate, and particularly the surface of the substrate to which the sample is introduced. The interface may be provided on a part of a side of the substrate, particularly a second side which opposes the first. The non-interface part of the side of the substrate may be in contact with a support, for instance a glass support.

The substrate may have a pH of 9+/− 1 pH unit. The pH may be provided at a pH which maximises the electrophoretic velocity of the analyte species in the substrate and/or minimises the electro-phoretic velocity of the analyte species in the second substrate and/or maximises the electro-osmotic velocity within the second substrate. The substrate is preferably neutral, particularly in terms of its surface charge. The substrate may be neutrally charged due to the use of neutral polymers and/or due to the neutralisation of the polymer charge by one or more additives. It is particularly preferred that no electro-osmotic flow occurs within the substrate.

The second substrate may have a pH of 9+/−1 pH unit. Preferably the pH of the second substrate is equivalent to the pH of the substrate. Preferably the buffer and/or the component the buffer is provided within, are provided so as to provide a high electro-osmotic velocity. The surface of the container may be conditioned, for instance through use of a pre-treatment with a strongly alkaline solution. Static and/or dynamic adjustment and/or coatings may be used to provide the desired level of electro-osmotic flow.

The electrical potential difference may be applied between a first electrode and a second electrode. Preferably the first electrode is in contact with the substrate, for instance the surface of a substrate and particularly the surface of the substrate to which the sample is introduced. The second electrode is preferably in contact with the second substrate, ideally a part of the second substrate removed from the interface.

Preferably the analyte species move towards the interface as a result of their electrophoretic velocity in the substrate. Preferably the analyte species move from their location of introduction to the substrate to the interface. Ideally the analyte species movement is not opposed by any electro-osmotic velocity within the substrate.

The bulk flow velocity may be caused and/or controlled by gravity, pressure or electro-osmotic properties.

Preferably the bulk flow velocity of the buffer equals or exceeds the electrophoretic velocity of the analyte species in the second substrate away from the concentrated band.

Preferably the electrophoretic velocity of the analyte species in the second substrate is balanced or exceeded by the electro-osmotic velocity of the second substrate is in an opposing direction to the electrophoretic velocity of the analyte species in the second substrate.

Preferably the electro-osmotic velocity of the second substrate equals or exceeds the electrophoretic velocity of the analyte species in the second substrate away from the concentrated band.

Preferably the method of collection is turned into a method of preparing a sample for analysis by reversing the polarity of electrical potential difference. The reversed electrical potential difference may be applied at the same potential difference or at a different potential difference to the initial electrical potential difference.

The application of the reversed electrical potential difference may occur after a time period without an electrical potential difference applied. The period without an electrical potential difference applied may be used to obtain diffusion of the analyte species away from the interface. Diffusion may occur away from the interface into the substrate, but more preferably occurs away from the interface into the second substrate. The period without the application of electrical potential difference may be for any time from zero up.

Preferably the reversing of the polarity of the electrical potential difference causes the electro-osmotic flow to be away from the interface. Preferably the electro-osmotic velocity conveys the analyte species away from the interface. The analyte species may be conveyed away from the interface all at substantially the same speed or at the same speed, particularly if the electro-osmotic flow predominates on all the analyte species. Preferably the concentration of the analyte species is maintained during movement away from the interface. Preferably the bulk flow velocity of the buffer is the electro-osmotic velocity. Preferably, the electro-osmotic velocity exceeds the electro-phoretic velocity of the analyte species in the second substrate during this part of the process.

The method of preparation may be extended to a method of analysing an analyte species from the sample, by conveying the analyte species in the second substrate away from the interface to an analysis location. The analysis location may be in the channel or container provided with the second substrate. The analysis may involve a consideration of the mobility of one or more of the analyte species in the buffer. Analysis conditions may be applied during the analysis part of the process. Analysis as an integral part of the apparatus is preferred, but the analyte species could be conveyed to a separate analysis process or apparatus.

Preferably extraction, enrichment of analysis of the analyte species is provided in a single piece of equipment and/or in a single method. Collection, concentration and analysis may be similarly provided.

The analysis technique may involve electrophoresis, such as gel electrophoresis or capillary electrophoresis, and/or chromatography.

Various embodiments of the present invention will now be described, by way of example only, and with reference to the accompanying drawings in which:

FIG. 5b illustrates in side view the chip of FIG. 5a; and

Figure 1:
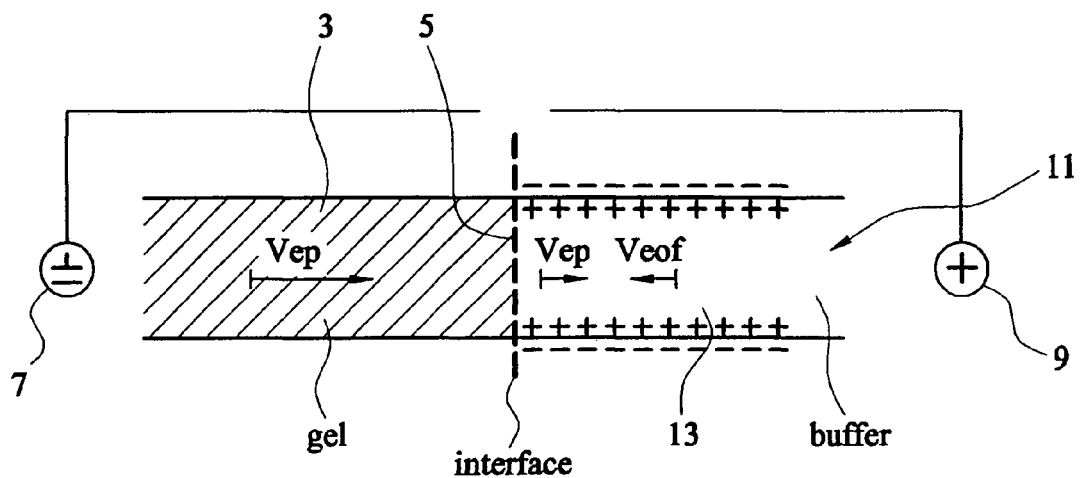
FIG. 1 illustrates the trapping stage of the present invention.

A variety of biological based investigations require the collection of as much as possible of an analyte species from a sample in which that analyte species is potentially widely dispersed. As high a recovery as possible of the analyte species from that raw sample is desirable to maximise the amount of analyte available for analysis and maximise the number of raw samples on which meaningful analysis can be performed.

As well as maximising the recovery of the analyte species it is also desirable for the concentration of analyte species in the prepared sample to be as high as possible. This will lead to a higher concentration in the media used for subsequent analysis.

Efficiency in collection and achieving high levels of concentration render an increased number of samples as candidates for examination using one or more existing analysis techniques. For instance high efficiency in recovery could lead to possibilities for analysing very small samples which are presently too small to give a sufficient feed to an analysis technique. For instance higher concentrations in the processed sample may allow the consideration of disease markers and proteins and potentially allow analysis techniques to be applied without requiring cell culture prior to analysis. Avoiding cell culturing allows pre-clinical analysis to be performed both faster and cheaper.

The collection and concentration of analyte species, for instance biochemical markers, is important in the context of forensic science also. For instance, identification of chemical substances present in a range of biological materials can yield valuable forensic intelligence on the lifestyle, sex and physiology of a perpetrator of a crime or person of interest. Such forensic intelligence is complementary to that obtained from DNA analysis, and so enables a broader description of the perpetrator and/or person of interest to be established.

The collection of chemical components of fingerprints is a further area of forensic interest. Additionally the developments offered by the present technique enable further research in this area to be conducted more effectively.

The development of quick, effective recovery and concentration systems also enables integrated chip-based systems to be used in rapid, in field determination of both biochemical and DNA profile.

Possibilities in terms of cheap, rapid, portable screening through very small quantities of drugs, drugs of abuse or their metabolites are also envisaged.

Various attempts have been made to improve electrophoretic based analysis techniques, such as gel electrophoresis and capillary electrophoresis, in terms of the preparation of the sample and/or the loading of the prepared sample into the analysis equipment.

WO 01/89667 and others, for instance, provide improved methods for loading substrates, such as gels. These prior art teachings us various chemical combinations and voltage profiles to increase the concentration of the prepared sample as it is loaded from a liquid buffer into the substrate to give the loaded sample.

Other techniques apply an electric potential to transfer analyte species from a substrate, such as a gel into a buffer and rely upon the lower electrophoretic velocity of the analyte species within the buffer to cause the analyte species to become closer together in the buffer and hence more concentrated. Such "stacking" techniques use a consistent polarity of electrical potential throughout with the stacked analyte species being continuously conveyed away from the gel as they leave the interface. Whilst such a technique provides some improvement in concentration, the present invention provides far greater improvements. Additionally such techniques require the analyte species to have a substantial electrophoretic velocity in the buffer, and as a consequence are only appropriate for highly charged analyte species. No electroosmotic flow is employed.

The present invention is concerned with improvements in efficiency and/or concentration which can be achieved prior to this in the generation of the prepared sample from the raw sample. Of course the techniques for improving the position when loading prepared samples into substrates can also be applied to the present invention, but it is preferred to perform the analysis in the buffer phase.

The technique is described in this example in relation to the collection and concentration of analyte species in the form of chemical residues from a fingerprint, but is very widely applicable to a full range of analyte species.

To collect the chemical residues from a fingerprint, the fingerprint is applied to a first surface 1 of a gel 3, as illustrated in 3. A potential difference is applied across the gel 3 between the first, contact surface 1 to the other surface 5 using electrodes, not shown. The potential difference causes the chemical residues to migrate from the first surface 1 through the gel 3 towards the second surface 5.

Figure 2:
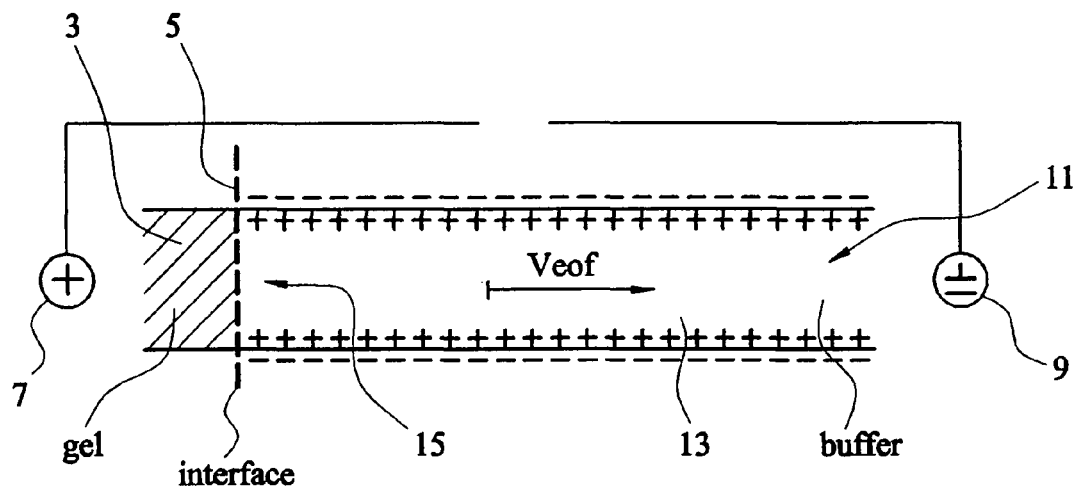
FIG. 2 illustrates the electro-osmotic injection stage of the present invention.

The operation of the technique is now described in relation to the more detailed, schematic illustrations of FIGS. 1 and 2. In most cases the residues to be collected are negatively charged at the pH provided by the gel 3. As a consequence the provision of a negative contact 7 on the first, contact, surface 1 of the gel 3, and a positive electrode 9 on the other side 11 promotes the movement of the analyte species away from the first surface 1 towards the second surface 5.

In gels best suited to the present invention there is no endoelectro-osmotic flow due to the careful selection of the gels used. In general, the gels feature polymers which are neutral or alternatively for which any charge present has been neutralised, for instance through the use of additives. Agar rose gels having such properties are widely available. In the absence of any endoelectro-osmotic flow, the analyte species migrates through the gel 3 at a velocity, V1, that corresponds to its electrophoretic velocity in the gel. Thus $V1=V_{ep1}=\mu_{ep}.E$, where $V_{ep}$ is the analyte species electrophoretic velocity, $\mu_{ep}$ is the electrophoretic mobility of the analyte species in the gel, and E is the electric field strength in $Vm^1$.

The second surface 5 of the gel 3 defines an interface between the gel 3 and a buffer 13 of equivalent pH. The electro-osmotic flow within the buffer 13 is high, and contributes most to the velocity of the analyte species in the buffer 13. Electro-osmotic flow is normally towards the cathode the provision of high electro-osmotic flow within the buffer is ensured by suitable design or treatment of the capillary and supporting system. Thus in the case of negatively charged particles, a highly alkaline solution may be used to pre-treat the channel and so condition it to have a generally positive charge associated with the internal surface. Alternatively coatings, dynamic adjustments or static adjustments could be used to achieve the same characteristics. If positively charge analyte species are of interest then it is straightforward to provide positive charge through alternative conditioning or treatment. Given this electro-osmotic flow within the buffer, observed apparent velocity, V2, of the analyte species in the buffer 13 is the vector resulting from the sum of the contributions present. In this case that is $V2=V_{ep2}+V_{eof}$, where $V_{ep2}$ is the analyte species electrophoretic velocity in the buffer, and $V_{eof}$ is the electro-osmotic velocity.

As the electrophoretic velocity of the analyte species in the buffer 13 is considerably smaller that its electrophoretic velocity in the gel 3, principally due to the high difference between the conductivity of the gel 3 and the buffer 13, the electrophoretic velocity in the buffer 13 is at least equalled by, but opposed in direction, by the electro-osmotic velocity. As a consequence V2 equals zero or is negative. The result of this is that the analyte species cannot move significantly beyond the interface and a concentrated mass of the analyte species builds up with time at the interface between the gel 3 and the buffer 13. In effect a trap is created for the analyte species at the point where the electrophoretic properties of the gel cease to apply, and the electrophoretic properties of the buffer begin to apply. The concentrating effect of this situation is far higher than the concentrating effect of stacking as the analyte species are fully retained at the interface; in stacking they move onward, but in a compressed from.

According to the mass conservation law, the flow in and out of the interface must be the same, i.e. $C_1V_1=C_2V_2$ where $C_1V_1$ and $C_2V_2$ are the concentration and the velocity of analyte species respectively in the gel 3 and in the buffer 13. As a result, $C_2\backslash C_1=V_1\backslash V_2$. As $V_2$ is effectively zero in principal the analyte species can be very highly enriched, $C_2$ approaches infinity, whilst the voltage difference is maintained.

The application of these conditions, therefore, for a moderate period of time enables the analyte species to be swept away from the contact surface towards the interface and retained and concentrated at that interface. Effective and complete collection of the analyte species is thus achieved and furthermore this is achieved at a greatly enhanced concentration of the analyte species in this prepared sample when compared with the raw sample. Beneficially the technique of the present invention is equally applicable to positive or negatively charged analyte species; all that is required is that the polarity of the electrical potential difference is configured to suit the analyte species of interest.

In the next stage, the potential difference is removed and diffusion of the concentrated analyte species is allowed. Diffusion can occur in both directions, but it is significantly faster in the direction of the buffer 13. As a result this stage allows the concentrated analyte species to move from the interface into the initial section 15 of the buffer 13. Controlling the diffusion time allows effective diffusion out of the gel 3, whilst limiting dispersion of the analyte species within the buffer 13 and hence dilution of the prepared sample.

The mobilisation of the concentrated, prepared sample and its transfer to the next stage of any technique is achieved by applying a potential difference of reversed polarity compared to that use in the collection/concentration stage. This is a significant different when compared with "stacking" techniques, therefore, in which the same polarity is used to concentrate and then move on the analyte species. The electro-osmotic injection for use in the subsequent analysis technique is thus generated. The electro-osmotic flow is far and away the dominant contributor to the velocity of the analyte species in the buffer 13, but on this occasion the polarity promotes the flow of the concentrated analyte species away from the gel/buffer interface and through the buffer 13. Laminar flow results in the integrity of the concentrated, prepared sample of the analyte species being maintained within the buffer 13.

Figure 3:
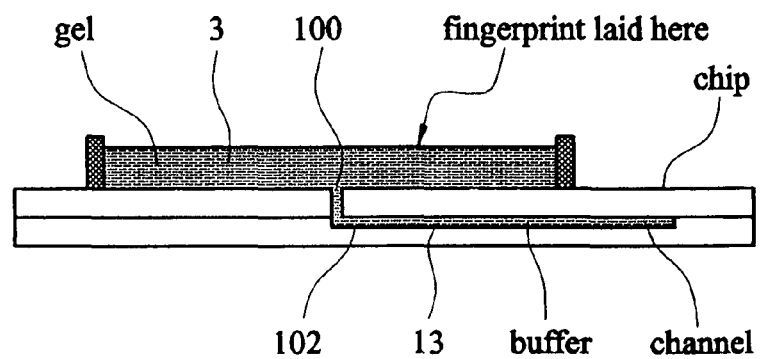
FIG. 3 illustrates a microchip based system for fingerprint collection.

The prepared sample can then be subject to separation and/or processing within the structure provided by the chip or other component embodying the process. Within the FIG. 3 form, the concentration and collection occurs at the interface 100 between the narrow channel 102 containing the buffer 13 and the gel 3. Once collected and mobilised the analyte species are moved along the channel 102 and the analysis is performed within the channel 102 for instance, by measuring differences in mobility for different analyte species in the electro-osmotic injection plug.

Importantly when compared with prior art techniques, it should be noted that the present method achieves a focussing and concentration of the analyte species rather than stacking. The voltage switched is used to mobilise the concentration band after the concentration and diffusion parts of the process. Over and above this it is also important to note that extraction, enrichment and analysis can all be performed in one device using the present invention. The relative dimensions of the substrate/gel and interface and buffer are also not critical in the present technique as the interface morphology is not relied upon to create an electrical potential drop or the like. The technique is also applicable to even small electrophoretic velocity, and as a consequence can be used for any charged component, not just those bearing a very significant charge. These benefits in a large part arise from the use of electro-osmotic flow in the buffer, a feature which is preferably entirely absent and indeed is possibly and deliberately avoided, in stacking methods.

Figure 4:
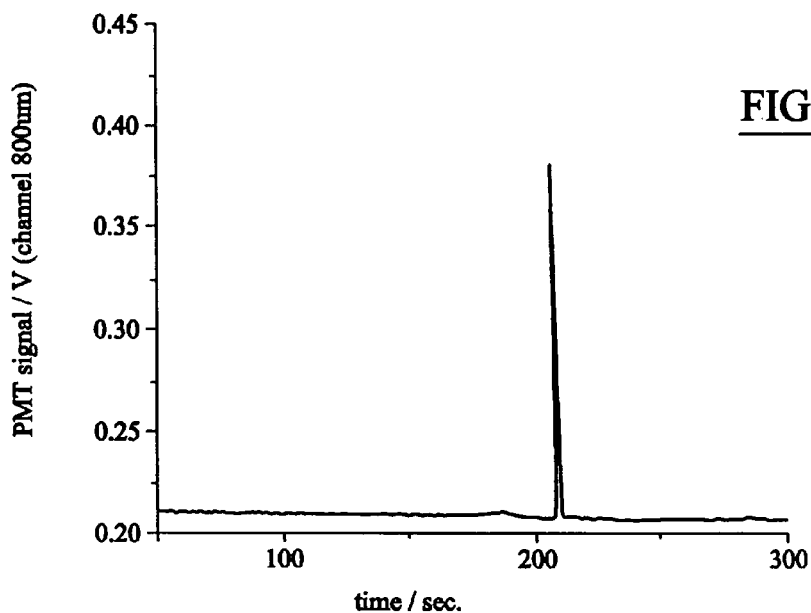
FIG. 4 illustrates the mobilisation of the concentration band arising from the concentration achieved by the present invention.

A measure of the efficiency of the electro-osmotic injection achieved can be seen in FIG. 4 by virtue of the concentration peak for the analyte species in that part of the buffer compared with its surroundings.

Figure 5A:
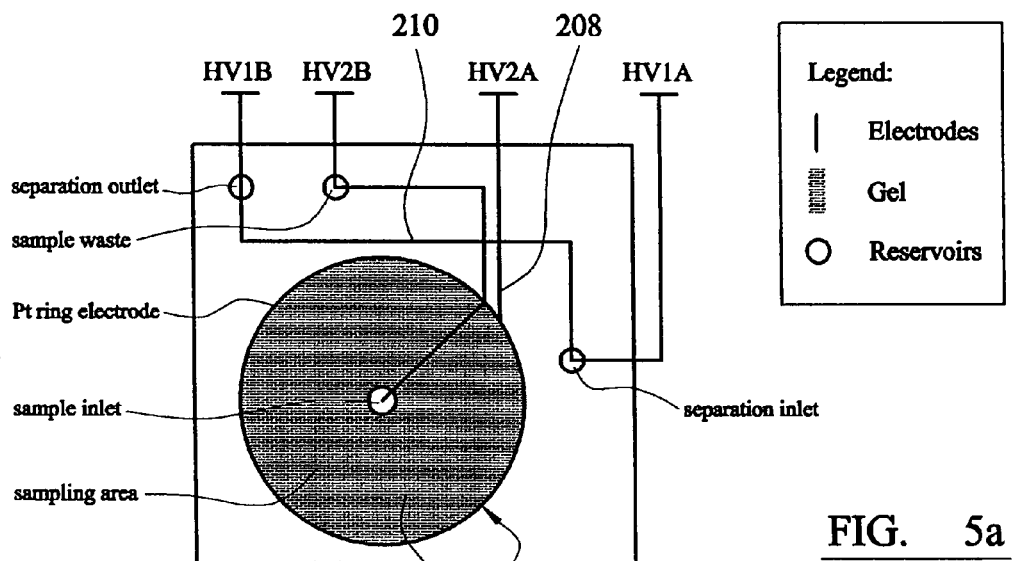
FIG. 5a illustrates in plan view a chip using the present invention.
Figure 5B:
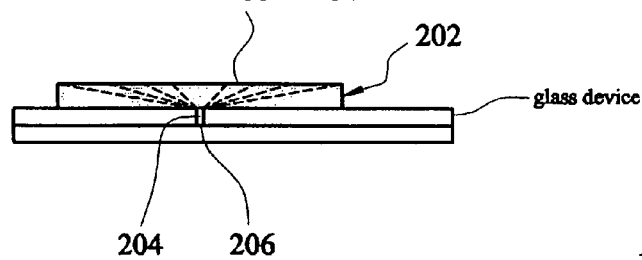

Within FIG. 5, an illustration of the use of such a technique to analyse fingerprints is provided. The fingerprint is applied to the top surface 200 of the gel 202, is collected from across the whole surface 202 and concentrated at the gel 200 to buffer 204 interface. This is at the top of a channel 206. Once collected and concentrated at this interface, the analyte species arising from the fingerprint are allowed to diffuse and then are drawn away from the interface by a reversal of the polarity of the potential difference. The concentrated analyte species are moved along channel 208 and analysed there. Alternatively they can then be directed along channel 210 to form the feed to an analytical technique, not shown.

Figure 6:
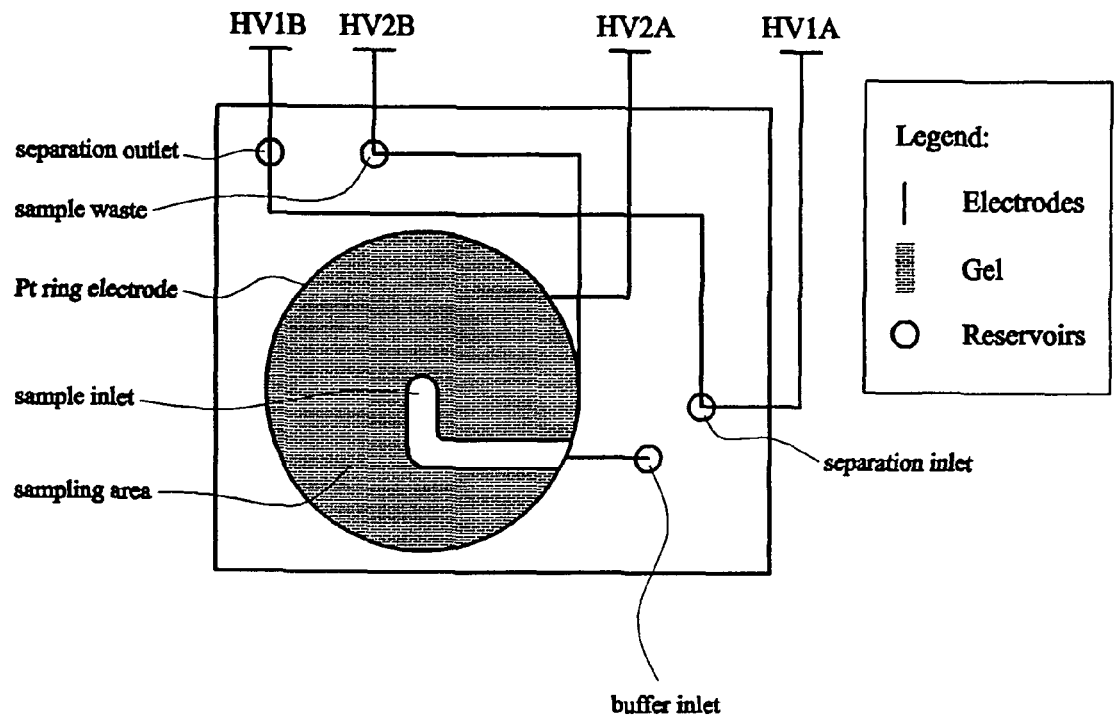
FIG. 6 illustrates an alternative chip design.

A further chip design is provided in FIG. 6 which offers still greater versatility and performance in applying the method of the present invention. It is preferred in this case that a further channel is provided. This channel provides an optional buffer inlet and ideally leads to close to the interface between the gel and the channel into which the analyte species are moved after collection. By introducing buffer to this channel at the time of the reversal of the polarity of the electrical potential the electric field strength/electrical potential can be maintained. This gives a faster movement of the analyte species away from the interface. The channel is shown in relief in FIG. 6 for the purposes of clarity.

Whilst the technique has been discussed above in the context of improvements in forensic analysis, the technique has wide ranging applicability. It can be used for instance in proteomics, clinical investigations, diagnostic investigations, pharmaceutical industries. A wide variety of situations occur in which as high as possible recovery of analyte species from a sample is desired, and the provision of such analyte species in concentrated form prior to analysis assists. Accuracy and/or speed and/or simplification in subsequent analytical techniques can be expected.

The invention claimed is:

1. A method of collecting an analyte species from a sample, the method including:—
    introducing at least a part of the sample to a substrate, the substrate having an interface with a second substrate;
    applying an electrical potential difference across at least a part of the substrate, the interface and at least a part of the second substrate, at least one of the analyte species in the substrate moving towards the interface as a result of the electrical potential difference to form collected analyte species;
    and wherein the electro-phoretic velocity of the analyte species in the second substrate is balanced by or exceeded by the bulk flow velocity of the second substrate and the bulk flow velocity of the second substrate is in an opposing direction to the electrophoretic velocity of the analyte species in the second substrate.

2. A method according to claim 1, wherein the method further provides a method of preparing a sample for analysis, the method including:
    reversing the electrical potential difference across the at least a part of the substrate, the interface and the at least part of the second substrate, the collected analyte species moving away from the interface and through the second substrate as a result of the electrical potential difference being reversed.

3. A method according to claim 2, wherein the analyte species in the second substrate are fed to an analysis stage, one or more pieces of information being determined about the analyte species by the analysis stage.

4. A method according to claim 2 in which the application of the reversed electrical potential difference occurs after a time period without an electrical potential difference applied, the period without an electrical potential difference applied is used to obtain diffusion of the analyte species away from the interface.

5. A method according to claim 1 in which the analyte species is one or more of a disease marker, a protein, a drug, a metabolite, a bio-chemical marker, a chemical residue, a chemical component of fingerprint or other body marks, a skin residue or an excretion or a plurality of such species or of different types of the same species.

6. A method according to claim 1 in which the interface between the substrate and the second substrate is provided on an opposing side of the substrate to the surface to which the sample is introduced.

7. A method according to claim 1 in which the pH is provided to maximise the electrophoretic velocity of the analyte species in the substrate.

8. A method according to claim 1 in which the pH is provided so as to minimise the electrophoretic velocity of the analyte species in the second substrate.

9. A method according to claim 1 in which the pH is provided so as to maximise the electro-osmotic velocity within the second substrate.

10. A method according to claim 1 in which the method further comprises reversing the polarity of electrical potential difference.

11. A method according to claim 1 in which the reversing of the polarity of the electrical potential difference causes the electro-osmotic flow to be away from the interface and the electro-osmotic velocity conveys the analyte species away from the interface.

12. A method of collecting an analyte species from a sample, the method including:
   introducing at least a part of the sample to a substrate, the substrate having an interface with a second substrate; and
   applying an electrical potential difference across at least a part of the substrate, the interface and at least a part of the second substrate, at least one of the analyte species in the substrate moving towards the interface as a result of the electrical potential difference to form collected analyte species;
   wherein the electro-phoretic velocity of the analyte species in the second substrate is balanced by or exceeded by the bulk flow velocity of the second substrate and the bulk flow velocity of the second substrate is in an opposing direction to the electrophoretic velocity of the analyte species in the second substrate; and
   wherein the substrate is a gel, the second substrate is a buffer, and the electrophoretic velocity of the analyte species in the buffer is balanced by or exceeded by the electro-osmotic velocity of the buffer and the electro-osmotic velocity of the buffer is in an opposing direction to the electrophoretic velocity of the analyte species of the buffer.

13. A method according to claim 12 in which the pH is provided to maximise the electrophoretic velocity of the analyte species in the substrate.

14. A method according to claim 12 in which the pH is provided so as to minimise the electrophoretic velocity of the analyte species in the second substrate.

15. A method according to claim 12 in which the pH is provided so as to maximise the electro-osmotic velocity within the second substrate.

16. A method according to claim 12, wherein the method further provides a method of preparing a sample for analysis, the method including reversing the electrical potential difference across the at least a part of the substrate, the interface and the at least part of the second substrate, the collected analyte species moving away from the interface and through the second substrate as a result of the electrical potential difference being reversed.

17. A method according to claim 16, wherein the method further provides a method of analysing an analyte species from a sample, wherein the analyte species in the second substrate are fed to an analysis stage, one or more pieces of information being determined about the analyte species by the analysis stage.

18. A method according to claim 17 in which the application of the reversed electrical potential difference occurs after a time period without an electrical potential difference applied, the period without an electrical potential difference applied is used to obtain diffusion of the analyte species away from the interface.

19. A method according to claim 16 in which the electro-osmotic velocity exceeds the electro-phoretic velocity of the analyte species in the second substrate when the polarity of the electrical potential difference is reversed.

20. A method according to claim 12 in which the reversing of the polarity of the electrical potential difference causes the electro-osmotic flow to be away from the interface and the electro-osmotic velocity conveys the analyte species away from the interface.

21. A method of preparing a sample for analysis, the method including:
   introducing at least a part of the sample to a substrate, the substrate having an interface with a second substrate;
   applying an electrical potential difference across at least a part of the substrate, the interface and at least a part of the second substrate, at least one of the analyte species in the substrate moving towards the interface as a result of the electrical potential difference to form collected analyte species,
   wherein the electro-phoretic velocity of the analyte species in the second substrate is balanced by or exceeded by the bulk flow velocity of the second substrate and the bulk flow velocity of the second substrate is in an opposing direction to the electrophoretic velocity of the analyte species in the second substrate; and
   reversing the polarity of electrical potential difference,
   wherein the electro-osmotic velocity exceeds the electro-phoretic velocity of the analyte species in the second substrate when the polarity of the electrical potential difference is reversed.

22. A method according to claim 21 in which the pH is provided to maximise the electrophoretic velocity of the analyte species in the substrate.

23. A method according to claim 21 in which the pH is provided so as to minimise the electrophoretic velocity of the analyte species in the second substrate.

24. A method according to claim 21 in which the pH is provided so as to maximise the electro-osmotic velocity within the second substrate.

* * * * *